(12) United States Patent
Ju et al.

(10) Patent No.: US 7,041,304 B2
(45) Date of Patent: May 9, 2006

(54) THERMOTROPIC LIQUID CRYSTAL POLYMER MICROCAPSULES, A METHOD FOR PREPARING THE SAME, AND COSMETIC COMPOSITIONS CONTAINING THE SAME

(75) Inventors: Hee Kyung Ju, Seoul (KR); Jin Woong Kim, Yongin-shi (KR); Sang Hoon Han, Suwon-shi (KR); Ih Seop Chang, Yongin-shi (KR); Han Kon Kim, Suwon-shi (KR); Hak Hee Kang, Seongnam-shi (KR); Ok Sub Lee, Anyang-shi (KR)

(73) Assignee: Pacific Corporation, Seoul (KR)

( * ) Notice: Subject to any disclaimer, the term of this patent is extended or adjusted under 35 U.S.C. 154(b) by 69 days.

(21) Appl. No.: 10/207,199

(22) Filed: Jul. 30, 2002

(65) Prior Publication Data

US 2003/0129247 A1    Jul. 10, 2003

(30) Foreign Application Priority Data

Oct. 19, 2001  (KR) ............................... 2001-64664
Feb. 28, 2002  (KR) ............................... 2002-10961

(51) Int. Cl.
*A61K 9/14*        (2006.01)

(52) U.S. Cl. ..................... 424/401; 424/489; 424/490; 264/4.1; 264/4.3; 264/4.33; 264/4.7

(58) Field of Classification Search ............ 424/78.03, 424/401, 489–490, 491, 492, 493, 497; 264/4.1, 264/4.3, 4.33, 4.7
See application file for complete search history.

(56) References Cited

U.S. PATENT DOCUMENTS

| 4,046,741 | A |   | 9/1977  | Scher ........................... 260/77.5 |
| 4,155,741 | A |   | 5/1979  | Scher et al. .................... 71/65 |
| 4,285,720 | A |   | 8/1981  | Scher ............................ 71/88 |
| 5,089,253 | A | * | 2/1992  | Halloran ....................... 424/47 |
| 5,744,148 | A |   | 4/1998  | Habif et al. ................... 424/401 |
| 5,851,538 | A |   | 12/1998 | Froix et al. ................... 424/401 |
| 5,985,296 | A |   | 11/1999 | Moldenhauer et al. ........ 424/401 |
| 6,174,467 | B1 |  | 1/2001  | Hsu |
| 6,183,774 | B1 |  | 2/2001  | Aust et al. .................... 424/450 |
| 2002/0055560 | A1 | * | 5/2002 | Nanbu et al. .................. 524/21 |

FOREIGN PATENT DOCUMENTS

DE    41 49 151 A1    6/1993

OTHER PUBLICATIONS

Ju et al., "Thermotropic liquid-crystal/polymer microcapsules prepared by in situ suspension polymeriztion", Colloid Polym Sci (2002), 280, pp. 879-885.

Kim, et al., "New Approach to Produce Monosized Polymer Microcapsules by the Solute Co-diffusion Method", Langmuir 2001, 17, pp. 5435-5439.

* cited by examiner

*Primary Examiner*—Gollamudi S. Kishore
(74) *Attorney, Agent, or Firm*—Nixon & Vanderhye P.C.

(57) ABSTRACT

There are provided thermotropic liquid crystal polymer microcapsules which can show behavior of liquid crystal as it is within polymer phase due to phase separation between liquid crystal and polymer, so to be incorporated into cosmetic composition as an additive for visual effect, and in loading active ingredients within liquid crystal, can improve the stability of the active ingredients in cosmetic base; and a method for preparing the same; and cosmetic compositions containing the same.

6 Claims, 4 Drawing Sheets

THERMOTROPIC LIQUID CRYSTAL POLYMER MICROCAPSULES, A METHOD FOR PREPARING THE SAME, AND COSMETIC COMPOSITIONS CONTAINING THE SAME

BACKGROUND OF THE INVENTION

1. Field of the Invention

The present invention relates generally to thermotropic liquid crystal polymer microcapsules, a method for preparing the same, and cosmetic compositions containing the same. More particularly, the present invention relates to thermotropic liquid crystal polymer microcapsules which can show behavior of a liquid crystal in the polymer phase due to phase separation between liquid crystal and polymer, therefore, can be incorporated into cosmetic composition as an additive for visual effect, and can improve the stability of the active ingredients in cosmetic base by loading the active ingredients within the liquid crystal, and relates to a method for preparing the same.

2. Description of the Related Arts

Liquid crystal shows unique arrangement in electric field, and therefore, it is used in display of electric apparatus such as projector, computer and television. Further, it has been incorporated in the cosmetic composition for improving protective function of stratum corneum and for increasing moisture retention and softness of the skin. Additionally, some liquid crystals, because of structural regularity, can scatter light to show beautiful colors and thereby provide unique appearance. Therefore, liquid crystals have been extensively used in the cosmetic field.

Conventionally, liquid crystals, in order to be protected from contaminants, oxidants and radiations or to provide novel functions, were encapsulated by polymers. And, extensive studies on encapsulation of liquid crystals have been conducted.

For examples, Japanese Patent Laid-open publication No. 61-502128 disclosed a method for encapsulating liquid crystal, which comprises steps of mixing liquid crystal with thermosetting resin, and then hardening the resin to be separated from liquid crystal. And, U.S. Pat. No. 4,285,720, No. 4,155,741 and No. 4,046,741 disclosed a method for preparing polyurea microcapsules by interfacial polymerization of polyisocyanate as an intermediate.

However, it is impossible to observe unique behavior of liquid crystal, i.e. orientation of liquid crystal in the microcapsules provided by these conventional methods, because liquid crystals are dispersed within polymer phase without separation thereof.

In addition, in case of thermotropic liquid crystal that was applied to smart system, because its behavior depends on environmental change such as temperature, the behavior became diluted by the addition of solvent or migration into hydrophobic phase, and therefore, sometimes encapsulation was impossible.

Under this circumstance, the present inventors have conducted extensive studies on encapsulation of liquid crystal of which behavior can be observed as it is. As a result thereof, we found that by encapsulating cholesterol-type thermotropic liquid crystal and monomer with suspension polymerization method, compatibility between liquid crystal material and polymer decreases in polymerizing process, which causes phase separation of liquid crystal within polymer phase, and thereby to produce capsule-type particles with thermotropic liquid crystal surrounded by polymer. The obtained microcapsules (capsule-type particles) can show behavior of liquid crystal as it is within polymer phase.

In addition, the present thermotropic liquid crystal polymer microcapsules can be applied as a stabilizing media for active ingredients by loading the active ingredients within the liquid crystal phase. In this case, by adding copolymer having crosslinkable functional group in suspension polymerization step, the polymer surrounding liquid crystal can be crosslinked, and the result, active ingredients within the liquid crystal can be completely protected from external irritation.

SUMMARY OF THE INVENTION

Therefore, one object of the present invention is to provide thermotropic liquid crystal polymer microcapsules showing the behavior of liquid crystal itself.

Another object of the present invention is to provide thermotropic liquid crystal crosslinked polymer microcapsules for completely stabilizing active ingredients.

A further another object of the present invention is to provide a method for preparing said microcapsules.

A further another object of the present invention is to provide a method for stabilizing active ingredients by using said microcapsules.

A further object of the present invention is to provide cosmetic compositions containing said microcapsules. Additionally, a further another object of the present invention is to provide cosmetic compositions containing said liquid crystal crosslinked polymer microcapsules, which can maintain efficiency of active ingredients for a long time.

These and other objects and advantages of the present invention will become apparent to the skilled in the art from the following detailed description as considered in conjunction with the accompanying drawings.

DETAILED DESCRIPTION OF THE INVENTION

The following is a detailed description of the present invention.

In order to achieve the above objects, the present invention is characterized in that thermotropic liquid crystal polymer microcapsules are obtained by suspension polymerization of thermotropic liquid crystal and monomer. In detail, a method for preparing thermotropic liquid crystal polymer microcapsules according to the present invention comprises the following steps of (1) dissolving thermotropic liquid crystal and monomer in a solvent and then adding initiator thereto;

(2) emulsifying the solution obtained from step (1) in aqueous phase in presence of dispersion stabilizer; and (3) suspension polymerizing the emulsion obtained from step (2) in presence of polymerization inhibitor, to give thermotropic liquid crystal polymer microcapsules.

In the above-mentioned method, compatibility between liquid crystal material and polymer may decrease in polymerizing process, which causes phase separation of liquid crystal within polymer phase and thereby to produce capsule-type particles with thermotropic liquid crystals surrounded by polymer. This phase separation enables the microcapsules to show the behavior of liquid crystal, i.e. orientation of liquid crystal as it is within polymer phase and thereby to exhibit visual effect. Therefore, the thermotropic liquid crystal polymer microcapsules of the present invention can be incorporated into cosmetic composition as an additive for visual effect.

In addition, the thermotropic liquid crystal polymer microcapsules of the present invention show the behavior of liquid crystal depending on temperature, and therefore can be applied to smart drug-delivery system with temperature-dependence. That is to say, the microcapsules cannot exhibit behavior of liquid crystal in high temperature, so to enhance fluidity and thereby to rapidly release drug. On the other hand, in low temperature, liquid crystal can delay release of drug. Therefore, the microcapsules of the present invention can be applied to drug-delivery system.

Further, the present thermotropic liquid crystal polymer microcapsules can be applied as a stabilizing media for active ingredients by loading the active ingredients within the liquid crystal phase. In this case, the active ingredients loaded within the present microcapsules can be doubly stabilized by liquid crystals and polymer. That is to say, the active ingredients may be firstly stabilized by fixation within liquid crystal due to the molecular arrangement, and doubly stabilized by polymer surrounding the liquid crystals. In this case, in order to elevate the stability of active ingredients, copolymer having crosslinkable functional group (hereinafter, "crosslinkable copolymer") may be added in step (1) of said method. The copolymer of the present invention can crosslink the polymer surrounding liquid crystals, and completely protect active ingredients within liquid crystal from external irritation.

Hereinafter, the present method for preparing thermotropic liquid crystal polymer microcapsules will be described in more detail.

Step (1) of Dissolving Thermotropic Liquid Crystal and Monomer in a Solvent and then Adding Initiator Thereto:

A thermotropic liquid crystal employed in this step is not restricted specifically and cholesterol-type liquid crystals or cholesteryl derivatives such as cholesteryl octanoate, cholesteryl nonanoate, cholesteryl oleyl carbonate and cholesteryl isostearyl carbonate are preferred.

Because cholesterol-type liquid crystal shows various colors depending on temperature or light angle and is harmless to human skin, it is useful as a cosmetic material.

Liquid crystal may be preferably used in an amount of 0.1~50% by weight based on the total weight of capsule particle. If the amount is less than 0.1 wt %, it may be impossible to observe behavior of liquid crystal. And, if the amount is more than 50 wt %, aimed product, i.e. microcapsules may not be obtained.

A monomer employed in the present invention may, if it is capable of radical polymerization, not be limited to specific kind. Preferably, it may be one or more selected from the group consisting of styrene, p- or m-methylstyrene, p- or m-ethylstyrene, p- or m-chlorostyrene, p- or m-chloromethylstyrene, styrenesulfonic acid, p- or m-t-butoxystyrene, methyl(meth)acrylate, ethyl(meth)acrylate, propyl (meth)acrylate, n-butyl(meth)acrylate, isobutyl(meth) acrylate, t-butyl(meth)acrylate, 2-ethylhexyl(meth)acrylate, n-octyl(meth)acrylate, lauryl(meth)acrylate, stearyl(meth) acrylate, 2-hydroxyethyl(meth)acrylate, polyethylene glycol (meth)acrylate, methoxypolyethylene glycol(meth)acrylate, glycidyl(meth)acrylate, dimethylaminoethyl(meth)acrylate, diethylaminoethyl(meth)acrylate, vinyl acetate, vinyl propionate, vinyl butyrate, vinyl ether, allylbutyl ether, allylglycidyl ether, (meth)acrylic acid, maleic acid, alkyl(meth) acrylamide and (meth)acrylonitrile.

Monomer may be preferably used in an amount of 50~99.9% by weight based on the total weight of capsule particle. If the amount is less than 50 wt %, it may be impossible to form microcapsules. And, if the amount is more than 99.9 wt %, it causes the amount of liquid crystal to decrease relatively, resulting in limiting behavior of liquid crystal.

In the post-crosslinking case, it may be preferably to use crosslinkable copolymer of which the crosslinkable functional group is in a range of 0.1~50% by weight based on the total weight of monomer. If the amount of crosslinkable functional group is less than 0.1 wt %, it may be impossible to obtain effect of crosslinking. And, if the amount is more than 50 wt %, hydrophilic group of particle surface may inhibit loading of active ingredients.

A monomer having crosslinkable functional group for post-crosslinking may be preferably monomer with silane group and capable of radical polymerization. More preferably, it may be one or more selected from the group consisting of trichlorovinylsilane, trimethoxyvinylsilane, triethoxyvinylsilane, vinyltriisopropoxysilane, vinyltri-t-butoxysilane, vinyltriphenoxysilane, vinyltriacetoxysilane, vinyltri(isobutoxy)silane, vinyltri(2-methoxyethoxy)silane, 8-oct-1-enyltrichlorosilane, 8-oct-1-enyl trimethoxysilane, 8-oct-1-enyltriethoxysilane, 6-hex-1-enyltrichlorosilane and 6-hex-1-enyltriethoxysilane.

Said crosslinkable copolymer may be preferably produced by dispersion polymerizing said monomer capable of radical polymerization and said monomer with crosslinkable functional group. This copolymer may undergo radical polymerization in formation of microcapsule and then, after formation of microcapsules, undergo post-crosslinking to form crosslinked network structure. Crosslinked network of polymer will be described later.

Further, as another method for crosslinking polymer, a crosslinking agent may be added in this step. A crosslinking agent added may, if it is capable of radical polymerization, not be limited to specific kind. Preferably, it may be selected from the group consisting of divinylbenzene, 1,4-divinyloxybutane, divinylsulfone, diallylphthalate, diallylacrylamide, triallyl(iso)cyanurate, triallyltrimellitate, (poly)ethylene glycol di(meth)acrylate, (poly)propylene glycol di(meth)acrylate, pentaerythritol tetra(meth)acrylate, pentaerythritol tri (meth)acrylate, pentaerythritol di(meth)acrylate, trimethylolpropane tri(meth)acrylate, dipentaerythritol hexa (meth)acrylate, dipentaerythritol penta(meth)acrylate and glycerol tri(meth)acrylate.

Below-described experimental examples show that crosslinked network of polymer can improve structural stability of microcapsule and block outflow of cholesterol phase. Therefore, appropriate crosslinking may be required. But, excessive crosslinking may cause severe deformation of liquid crystal/polymer droplet. And, in case that microcapsule may be used as a stabilizing tool of active ingredients, crosslinked network of polymer may hinder active ingredients from loading within microcapsule. Therefore, in the present invention, it may be preferable to limit the amount of crosslinking agent employed in a range of 0.1~0.3% by weight based on the total weight of monomer.

As a solvent for dissolving said liquid crystal and said monomer, it may be unmixable with water and preferably have low or common melting point. More preferably, it may be haloalkane such as chloromethane, dichloromethane, chloroform, tetrachloromethane and dichloroethane, ethyl acetate, diethyl ether, cyclohexane, benzene, toluene, etc.

In order to dissolve said liquid crystal and monomer uniformly, it may be performed under irradiation of ultrasonic wave.

Further, an initiator is added in this step in order to initiate polymerization reaction. As an initiator employed in the present invention, it may be peroxides such as benzoyl peroxide, lauryl peroxide, o-chlorobenzoyl peroxide, o-methoxybenzoyl peroxide, t-butylperoxy-2-ethylhexanoate, t-butylperoxy isobutyrate, 1,1,3,3-tetramethylbutylperoxy-2-ethylhexanoate, dioctanoyl peroxide and didecanoyl peroxide; and azo compounds such as 2,2-azobisisobutyronitrile, 2,2-azobis(2-methylbutyronitrile) and 2,2-azobis(2,4-dimethylvaleronitrile).

In consideration of initiation efficiency, initiator may be preferably used in an amount of 1~2% by weight based on the total weight of monomer. That is, in a concentration of less than 1 wt %, though polymerization may be possible, it takes long time to obtain 90% or more of polymerization degree. And, in a concentration of more than 2 wt %, suddenly increased polymerization rate may break spherical liquid crystal and produce polymer having low molecular weight.

Step (2) of Emulsifying the Solution of Step (1) in Aqueous Phase in Presence of Dispersion Stabilizer:

A dispersion stabilizer employed in this step may be water-soluble polymer. Preferably, it may include gelatin, starch, hydroxyethyl cellulose, carboxymethyl cellulose, polyvinylpyrrolidone, polyvinylalkyl ether, polyvinyl alcohol, polydimethyl siloxane/polystyrene block copolymer, etc. It may be employed in an amount enough to inhibit polymer capsules obtained in dispersion polymerization from precipitating or agglutinating by gravity. Preferably, it may be added in an amount of 1~5% by weight based on the total weight of reactant. If the amount is less than 1 wt %, stabilization efficiency may suddenly decrease. And, if the amount is more than 5 wt %, viscosity of the system may increase and stabilization efficiency may come to equilibrium state, not to contribute stabilization.

Step (3) of Suspension Polymerizing the Emulsion of Step (2) in Presence of Polymerization Inhibitor, to Give Thermotropic Liquid Crystal Polymer Microcapsules:

Suspension polymerization must be performed in emulsion, but, in this step, emulsion particles are dispersed in aqueous phase. In this case, if polymerization reaction is initiated in aqueous phase, microcapsules may not be formed efficiently and particle size may be very small. Accordingly, in order to control polymerization in aqueous phase, it may be preferable to employ polymerization inhibitor.

A polymerization inhibitor employed in the present invention may, if it is soluble in aqueous phase, not be limited to specific kind. Preferably, it may be inorganic inhibitor such as hydroxylamine, hydrazine, sodium nitrate and potassium nitrate; or organic inhibitor such as hydroquinone, hydroquinone monomethyl ether and pyrocatechol. It may be preferably used in an amount of 0.01 wt % or less based on the total weight of reactant. That is because initiation efficiency may decrease in concentration of more than 0.01 wt % and thereby suspension polymerization may not proceed at all.

Suspension polymerization may be performed by a conventional method in this art.

In addition, microcapsules obtained in the above-described method have hydrophobic property and thereby, cannot be hydrated in aqueous solution. So, it may be impossible to observe behavior of liquid crystal in aqueous cosmetic base, which may contain the present microcapsules. In this case, it may be preferable to employ hydrated microcapsules.

Hydrated microcapsules may be obtained by addition of cationic monomer, anionic monomer or hydrophilic monomer. In detail, cationic monomer such as aminoalkyl(meth) acrylate or anionic monomer such as acrylic acid, methacrylic acid, maleic acid, fumaric acid, itaconic acid and sulfonic acid may be added in an amount of 10~30% by weight based on the total weight of monomer. Further, hydrophilic monomer such as acrylonitrile, methacrylonitrile, acrylamide and methacrylamide may be added in an amount of 10~50% by weight based on the total weight of monomer.

Thermotropic liquid crystal polymer microcapsules obtained in the above described method have the structure of liquid crystal material surrounded by polymer, to show behavior of liquid crystal as it is and so to provide visual effect. Therefore, the present liquid crystal polymer microcapsules can be incorporated into cosmetic composition as an additive for visual effect. The cosmetic compositions containing the microcapsules of the present invention may be formulated, but not limited thereto, as skin softners, nutrient toilet water, massage creams, nutrient creams, packs, jells, essences, lipsticks, make-up bases, foundation, lotions, ointments, gels, creams, patches or spray.

Further, because behavior of liquid crystal depends on temperature, the liquid crystal polymer microcapsules of the present invention may be applied to smart drug-delivery system having temperature-dependence.

Step (4) of Loading Active Ingredients in Liquid Crystal Polymer Microcapsule:

Further, the present thermotropic liquid crystal polymer microcapsules can be applied as a stabilizing tool of active ingredients by loading within liquid crystal phase.

When active ingredients are exposed to external irritation such as light, heat or water, most of them may lose their activities rapidly. In particular, active ingredients to impart special function to cosmetics may be easily deteriorated by surfactants, water or oily ingredients in cosmetic base. Accordingly, there is need to block said external irritation.

If active ingredients are loaded within the microcapsules of the present invention, they can be doubly stabilized by cholesterol-type liquid crystal and thereof outer polymer. That is to say, the active ingredients may be firstly stabilized by fixation within liquid crystal in thereof molecular arrangement, and doubly stabilized by polymer surrounding the liquid crystal.

In this case, by addition of crosslinkable copolymer in step (1) of said method, the polymer surrounding liquid crystals can be crosslinked, so to completely protect active ingredients within liquid crystal from external irritation and thereby, to elevate the stability of active ingredients.

A functional active ingredient loaded within the present microcapsules may be retinol, retinyl acetate, retinyl palmitate, tocopherol, tocopheryl acetate, tocopheryl linolate, tocopheryl nicotinate, linoleic acid, coenzyme Q-10, resveratrol, plant-extracting essential oil, etc.

As a method for loading active ingredients, the solute co-diffusion method disclosed in Korean Patent Appln. No. 2000-58991 may be applied.

In detail, the solute co-diffusion method comprises the following steps of (4-1) dissolving active ingredients in a solvent of enough amount for swelling the microcapsules of step (3), and then emulsifying in aqueous solution;

(4-2) dispersing the microcapsules of step (3) in aqueous solution with surfactant dissolved in proper concentration; and (4-3) adding the emulsion particles of step (4-1) into the dispersion of step (4-2), to load said active ingredients within said microcapsule particles.

Step (5) of Crosslinking Liquid Crystal Polymer Microcapsules

In case that crosslinkable copolymer may be added in step (1) of said method in order to elevate stability of the active ingredients loaded in step (4), crosslinked network may be formed by means of silane group of the copolymer in this step.

As above-described, crosslinked network of polymer may be formed by adding proper crosslinking agent in formation of microcapsules. But, in this case, crosslinked network may cause severe deformation of liquid crystal/polymer droplet and may hinder active ingredients from loading within microcapsules. So, the amount of crosslinking agent employed must be limited in specific range. Accordingly, it may be more preferable to form crosslinked network in post-crosslinking process by means of silane group of copolymer. Silane-crosslinking reaction can be performed in aqueous phase of room temperature, not in organic solvent, and so active ingredients loaded within the microcapsules can maintain their activities. Therefore, silane-crosslinking reaction can be preferably applied to crosslinking of microcapsules loading active ingredients. In order to promote silane-crosslinking reaction, an acid such as acetic acid, sulfonic acid and phosphoric acid; or a base such as ammonia may be added.

PREFERRED EMBODIMENT OF THE INVENTION

The present invention will be described in more detail by way of the following examples, which should not be considered to limit the scope of the present invention.

EXAMPLE 1

30 wt % of cholesteryl nonanoate and 70 wt % of methylmethacrylate monomer were dissolved uniformly in 20 ml of methylene chloride under irradiation of ultrasonic wave. As an initiator, 2,2'-azobis(2-methylbutyronitrile) was added thereto in an amount of 1 wt % based on the weight of monomer. The obtained solution was added into 1.5% aqueous solution of polyvinyl alcohol with 87~89% of saponification value and then was emulsified under 5,000 rpm of shear stress for 5 minutes. The emulsion and 0.01 wt % of sodium nitrate were introduced into the reactor heated at 60° C. and then polymerized for 4 hours. After the polymerization was terminated, the organic solvent was evaporated off under reduced pressure. The residue was filtrated, washed with distilled water several times, and then dried on vacuum oven, to give cholesterol liquid crystal polymer microcapsules as powders.

EXAMPLE 2

The procedure described in Example 1 was followed, except that as a crosslinking agent, ethylene glycol dimethyl ether was dissolved in an amount of 0.3 wt % based on the weight of monomer in methylene chloride, to give cholesterol liquid crystal polymer microcapsules.

COMPARATIVE EXAMPLE 1

The procedure described in Example 2 was followed, except that cholesteryl nonanoate liquid crystal was not added, to give polymer microcapsules.

COMPARATIVE EXAMPLE 2

The procedure described in Example 2 was followed, except that the crosslinking agent was added in an amount of 1.0 wt % based on the weight of monomer, to give cholesterol liquid crystal polymer microcapsules.

EXAMPLE 3

The procedure described in Example 2 was followed, except that 15 wt % of methacrylic acid was added to methylmethacrylate monomer, to give cholesterol liquid crystal polymer microcapsules.

EXAMPLE 4

The procedure described in Example 2 was followed, except that 20 wt % of vinyl acetate was added to methylmethacrylate monomer, to give cholesterol liquid crystal polymer microcapsules.

EXAMPLE 5

The procedure described in Example 2 was followed, except that 30 wt % of acrylonitrile was added to methylmethacrylate monomer, to give cholesterol liquid crystal polymer microcapsules.

EXAMPLE 6

Retinol was loaded within the cholesterol liquid crystal polymer microcapsules obtained in Example 2 by means of solute-co-diffusion method.

In detail, 0.5 g of retinol was completely dissolved in 20 ml of methylene chloride, and then added into 80 ml of water/ethanol solution with 0.25 wt % of sodium lauryl sulfate dissolved. Then, the mixture was emulsified under 25,000 rpm of shear stress for 5 minutes. Further, 9 g of liquid crystal polymer microcapsules obtained in Example 2 was dispersed in 100 ml of water/ethanol solution with 0.25 wt % of sodium lauryl sulfate dissolved, and then as a dispersion stabilizer, polyvinyl alcohol was added thereto in an amount of 1% based of the total weight. The retinol emulsion was added into the microcapsule dispersion, and then reacted at room temperature for 4 hours. The organic solvent was evaporated off under reduced pressure. The residue was filtrated, washed with distilled water several times, and then dried on vacuum oven, to give microcapsules as powders.

EXAMPLE 7

The procedure described in Example 6 was followed, except that as an active ingredient, coenzyme Q-10 was used in an amount of 10 wt % based on the total weight of microcapsule, to give microcapsules.

EXAMPLE 8

The procedure described in Example 6 was followed, except that as an active ingredient, tocopherol was used in an amount of 10 wt % based on the total weight of microcapsule, to give microcapsules.

EXAMPLE 9

The procedure described in Example 1 was followed except that crosslinkable copolymer was added in step (1), to give cholesterol liquid crystal polymer microcapsules. And then, retinol was loaded in the same procedure described in Example 6. After, post-crosslinking process was performed, to give cholesterol liquid crystal crosslinked polymer microcapsules as powders. The crosslinkable copolymer was produced by the following method, and each step will be described hereinafter.

(9-1) Preparation of the Crosslinkable Copolymer:

Firstly, methylmethacrylate 9 g, vinylsilane monomer 1 g, as an oil-soluble initiator, azobisisobutyronitrile 0.15 g and as a dispersion stabilizer, polyvinylpyrrolidone K-30 (molecular weight: 4,000 g/mol) 4 g were completely dissolved in 100 ml of methanol. Subsequently, polymerization was performed by stirring under conditions of 45~65° C., 40 rpm and nitrogen atmosphere, for 24 hours. The resulting solution was centrifuged to remove residue reactant and dispersion stabilizer and then dried on vacuum oven for 24 hours, to give, as silane copolymer, poly(methylmethacrylate-co-vinyl silane) 7.5 g as powders.

(9-2) Preparation of Liquid Crystal Polymer Microcapsules:

The obtained silane copolymer 7.2 g, cholesteryl nonanoate 8 g and methylmethacrylate monomer 72 g were dissolved uniformly in 20 ml of methylene chloride under irradiation of ultrasonic wave. And then, the procedure described in Example 1 was followed, to give cholesterol liquid crystal polymer microcapsules 80 g as powders.

(9-3) Loading of Retinol:

The procedure described in Example 6 was followed except that 1 g of retinol were employed to load retinol within the microcapsules.

(9-4) Formation of Crosslinked Network of Polymer:

After the above loading, in order to accelerate formation of crosslinked network, small quantity (about 0.05 g) of ammonia was added, and then the reaction was maintained for 1 hour. The organic solvent was evaporated off under reduced pressure. Subsequently, the residue was filtrated, washed with distilled water several times, and then dried on vacuum oven, to give microcapsules as powders.

EXAMPLE 10

The procedure described in Example 9 was followed, except that as an active ingredient, 1 g of coenzyme Q-10 was used instead of retinol, to give microcapsules.

EXAMPLE 11

The procedure described in Example 9 was followed, except that as an active ingredient, 2.5 g of tocopherol was used instead of retinol, to give microcapsules.

COMPARATIVE EXAMPLE 3

The procedure described in Example 9 was followed by employing only methylmethacrylate monomer, without cholesterol-type liquid crystal and silane group, to give microcapsules of polymer particles.

EXPERIMENTAL EXAMPLE 1

Morphology of the Microcapsules

Morphology of the microcapsules obtained in Examples 1~2 and Comp. Examples 2 was observed by optical microscope. And, phase behavior of liquid crystal was observed by polarizing microscope. The results are shown in FIGS. 1 to 3.

Figure 1A:
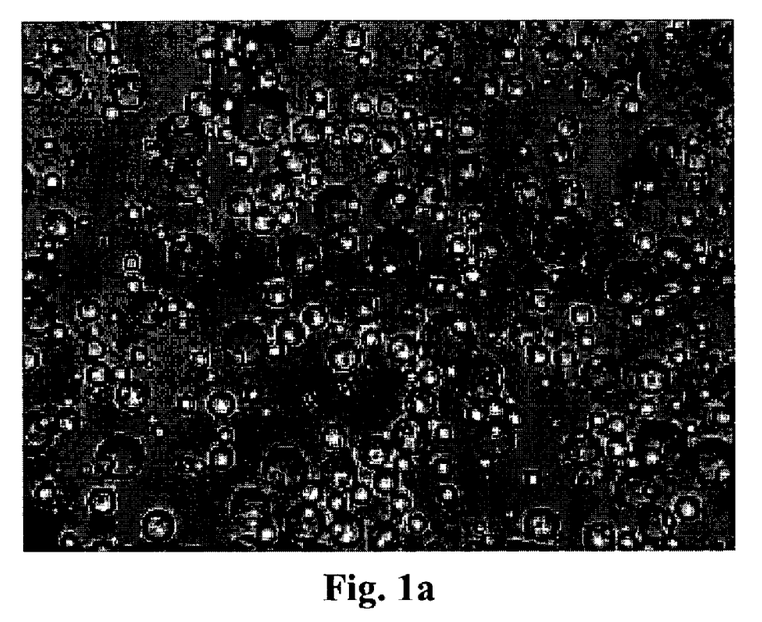
FIG. 1a is an optical microphotograph showing the microcapsules obtained in Example 1 (×500).
Figure 1B:
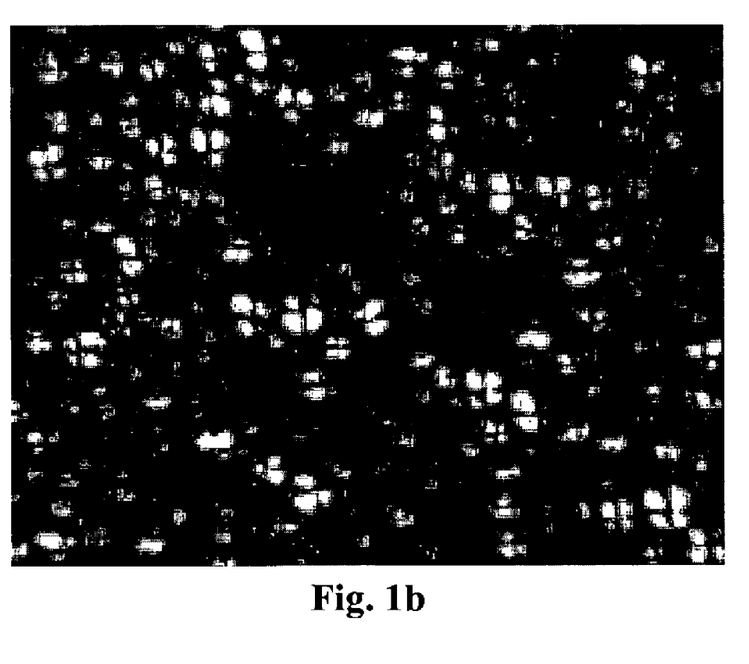
FIG. 1b is a polarizing microphotograph showing the microcapsules obtained in Example 1 (×500).
Figure 2A:
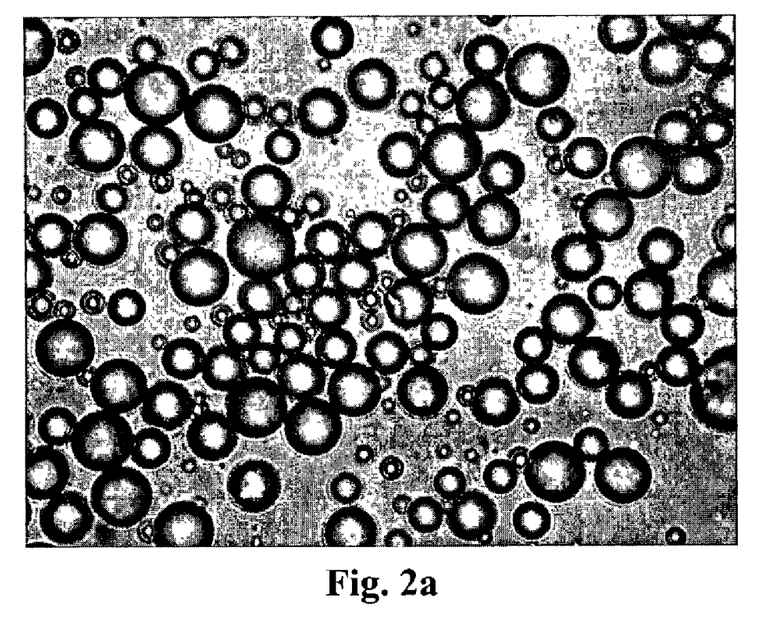
FIG. 2a is an optical microphotograph showing the microcapsules obtained in Example 2 (×500).
Figure 2B:
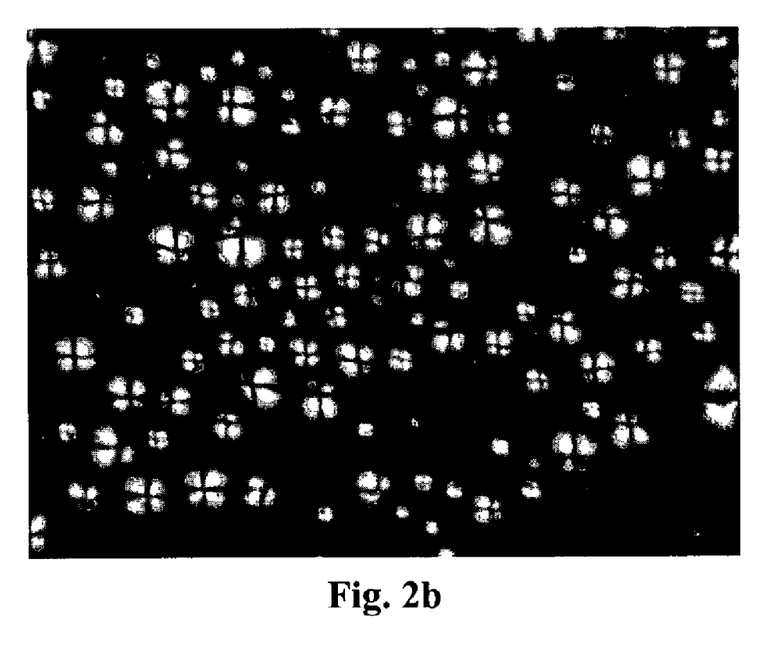
FIG. 2b is a polarizing microphotograph showing the microcapsules obtained in Example 2 (×500).
Figure 3A:
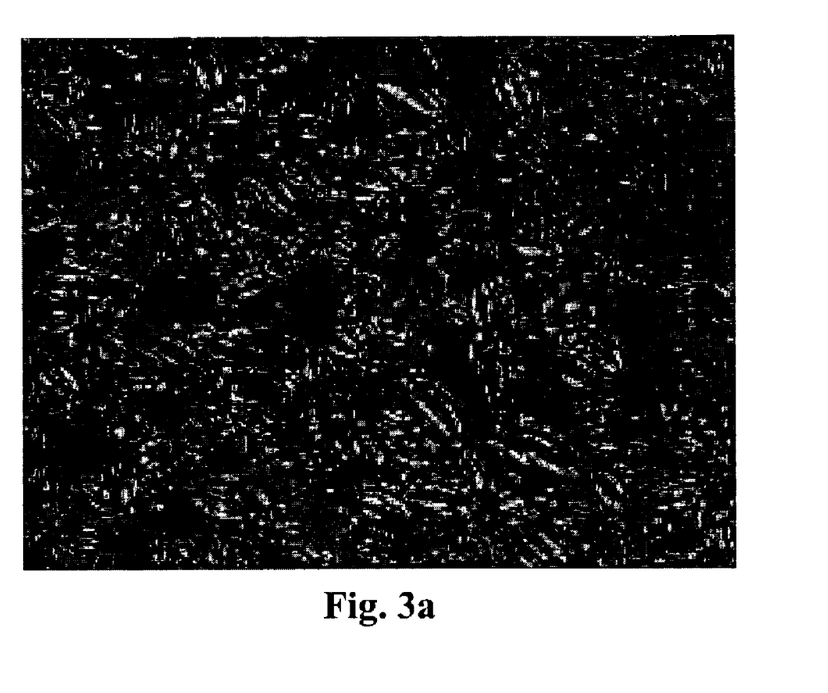
FIG. 3a is an optical microphotograph showing the microcapsules obtained in Comparative Example 2 (×500).
Figure 3B:
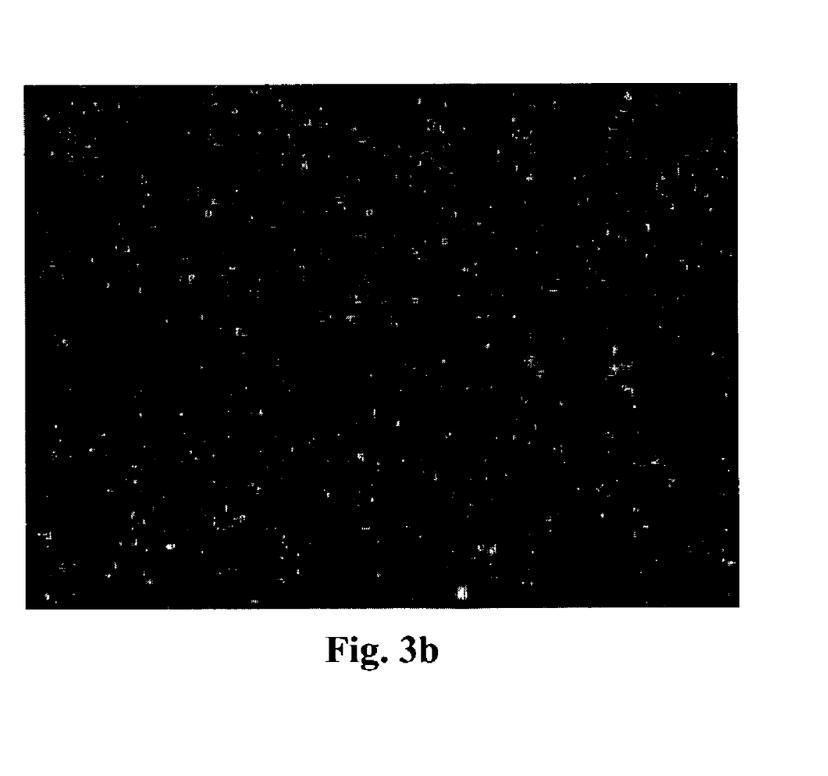
FIG. 3b is a polarizing microphotograph showing the microcapsules obtained in Comparative Example 2 (×500).

Further, FIGS. 1~3 show that morphology of the particles depends on crosslinking degree. That is, crosslinking of polymer may induce elastic force between crosslinked chains, to cause shrinkage of liquid crystal/polymer droplet. Accordingly, the droplet cannot maintain its initial sphere and may be deformed. Though the obtained microcapsules may not be sphere by deformation of the droplet, the crosslinked polymer phase can improve structural stability of the microcapsules and block outflow of inner cholesterol phase. Therefore, appropriate crosslinking may be required and the present invention may employ a crosslinking agent in an amount of 0.1~0.3 wt % based on the total weight of monomer.

EXPERIMENTAL EXAMPLE 2

The silane copolymers obtained by changing amount of monomer in Example 9 were analyzed by means of gel permeation chromatography and differential scanning calorimeter.

In result, molecular weights of the copolymers are in a range of 40000~50000 g/mol and glass transition temperature are in a range of 130~110° C. The glass transition temperature decreases in inverse proportion to increase in amount of silane group employed. The results are shown in Table 1. According to the results, the present invention employed the copolymers having 10 wt % of silane group based on the total weight of monomers.

TABLE 1

| Amount of monomer having silane group (wt %) | Molecular weight (g/mol) | Glass transition temperature (° C.) |
| --- | --- | --- |
| 0 | 43300 | 128.8 |
| 5 | 48400 | 122.8 |
| 10 | 50000 | 117.9 |
| 20 | 40000 | 114.9 |

Figure 4:
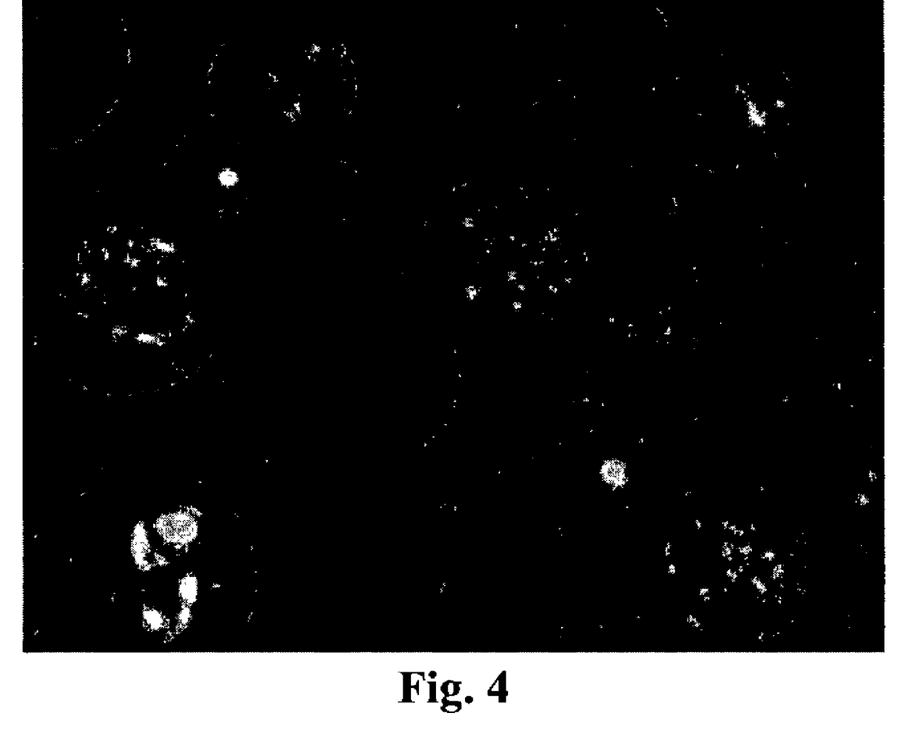
FIG. 4 is a con-focal laser scanning microphotograph showing distribution of retinol within the liquid crystal crosslinked polymer microcapsules obtained in Example 9.

Distribution of retinol loaded within the liquid crystal crosslinked polymer microcapsules obtained in Example 9 was observed by means of con-focal laser scanning microscope. FIG. 4 shows that self-fluorescent retinol is well distributed within the microcapsule particles. Retinol has similar molecular structure to that of cholesteryl nonanoate, i.e. liquid crystal material and thereby, can be stabilized by participating in molecular arrangement of liquid crystal and by fixation within liquid crystal.

In FIG. 4, all the particles do not show fluorescence of retinol. That is because each focus of the particle is different. The results confirmed that retinol is well distributed within liquid crystal phase of the polymer particles.

EXPERIMENTAL EXAMPLE 3

Each microcapsule obtained in Examples 2~5 was added into the following formulation and then behavior of liquid crystal was observed.

Formulations 1~4: Transparent Gel Type Soluble Formulation

Transparent gel type soluble formulations having the following composition of Table 2 were prepared. Viscosity of the formulation is about 3,000 cps. The viscosity was measured by means of Brookfield (LVDVII+) at a temperature of 30° C., under 12 rpm.

TABLE 2

| Materials | Formulation 1 | Formulation 2 | Formulation 3 | Formulation 4 |
|---|---|---|---|---|
| Glycerine | 5 | 5 | 5 | 5 |
| Propylene glycol | 4 | 4 | 4 | 4 |
| Microcapsule | | | | |
| Ex. 2 | 5 | — | — | — |
| Ex. 3 | — | 5 | — | — |
| Ex. 4 | — | — | 5 | — |
| Ex. 5 | — | — | — | 5 |
| Ethanol | 10 | 10 | 10 | 10 |
| Sodium polyacrylate | 0.5 | 0.5 | 0.5 | 0.5 |
| Preservative | q.s. | q.s. | q.s. | q.s. |
| Distilled water | to 100 | to 100 | to 100 | to 100 |

Formulations 5~8: Suspended Emulsion Type Lotion

Each of oily phase and aqueous phase in the following composition was completely dissolved at a temperature of 70° C., and then emulsified under 7,000 rpm for 5 minutes, to produce opaque gel type lotion. Viscosity of the lotion is about 2,000 cps.

TABLE 3

| Materials | Formulation 5 | Formulation 6 | Formulation 7 | Formulation 8 |
|---|---|---|---|---|
| Stearic acid | 2 | 2 | 2 | 2 |
| Cetyl alcohol | 2 | 2 | 2 | 2 |
| Lanolin alcohol | 2 | 2 | 2 | 2 |
| Liquid paraffin | 7 | 7 | 7 | 7 |
| Cyclomethicone | 5 | 5 | 5 | 5 |
| Polyoxyethylene monooleic ester | 2 | 2 | 2 | 2 |
| Preservative, Antioxidant | q.s. | q.s. | q.s. | q.s. |
| Glycerine | 3 | 3 | 3 | 3 |
| Propylene glycol | 5 | 5 | 5 | 5 |
| Triethylamine | 1 | 1 | 1 | 1 |
| Microcapsule | | | | |
| Ex. 2 | 8 | — | — | — |
| Ex. 3 | — | 8 | — | — |
| Ex. 4 | — | — | 8 | — |
| Ex. 5 | — | — | — | 8 |
| Sodium polyacrylate | 0.15 | 0.15 | 0.15 | 0.15 |
| Distilled water | to 100 | to 100 | to 100 | to 100 |

The microcapsules obtained in Example 2 could not be hydrated in aqueous solution by hydrophobic property of polymethylmethacrylate surrounding the cholesterol liquid crystal. So, behavior of liquid crystal within the polymer particles could not be observed. On the other side, the microcapsules obtained in Examples 3~5 exhibited behavior of liquid crystal in cosmetic formulation. Such a visual effect of liquid crystal can impart peculiarity to cosmetic composition and brilliance to appearance of goods, to be expected to elevate commercial value.

EXPERIMENTAL EXAMPLE 4

In order to evaluate stability of the active ingredients loaded in the liquid crystal polymer microcapsules obtained in Examples 6~11 and Comp. Example 3, creams were formulated in the following compositions of Table 4.

TABLE 4

| Materials | Formulations | | | | | | Comparative Formulations | |
|---|---|---|---|---|---|---|---|---|
| | 9 | 10 | 11 | 12 | 13 | 14 | 1 | 2 |
| Bee's wax | 2 | 2 | 2 | 2 | 2 | 2 | 2 | 2 |
| Stearyl alcohol | 5 | 5 | 5 | 5 | 5 | 5 | 5 | 5 |
| Stearic acid | 8 | 8 | 8 | 8 | 8 | 8 | 8 | 8 |
| Squalane | 10 | 10 | 10 | 10 | 10 | 10 | 10 | 10 |
| Propylene glycol monostearate | 3 | 3 | 3 | 3 | 3 | 3 | 3 | 3 |
| Polyoxyethylene cetyl ether | 1 | 1 | 1 | 1 | 1 | 1 | 1 | 1 |
| Preservative, Antioxidant | q.s. | q.s. | q.s. | q.s. | q.s. | q.s. | q.s. | q.s. |
| Propylene glycol | 8 | 8 | 8 | 8 | 8 | 8 | 8 | 8 |
| Glycerine | 4 | 4 | 4 | 4 | 4 | 4 | 4 | 4 |
| Triethylamine | 1 | 1 | 1 | 1 | 1 | 1 | 1 | 1 |
| Microcapsule | | | | | | | | |
| Ex. 6 | 2 | — | — | — | — | — | — | — |
| Ex. 7 | — | 2 | — | — | — | — | — | — |
| Ex. 8 | — | — | 2 | — | — | — | — | — |
| Ex. 9 | — | — | — | 2 | — | — | — | — |
| Ex. 10 | — | — | — | — | 2 | — | — | — |
| Ex. 11 | — | — | — | — | — | 2 | — | — |
| Comp. Ex. 3 | — | — | — | — | — | — | 2 | — |

TABLE 4-continued

|  | Formulations | | | | | | Comparative Formulations | |
|---|---|---|---|---|---|---|---|---|
| Materials | 9 | 10 | 11 | 12 | 13 | 14 | 1 | 2 |
| Retinol (not-encapsulated) | — | — | — | — | — | — | — | 2 |
| Distilled water | to 100 | to 100 | to 100 | to 100 | to 100 | to 100 | to 100 | to 100 |

Not-encapsulated retinol was 50C (BASF Co.) as an article on the market.

Each test sample of the formulations was preserved on the ovens of 25° C. and of 40° C. for prescribed period. After, the residue active ingredient in the sample was measured by means of liquid chromatography. The results are shown in Table 5.

TABLE 5

|  | Microcapsules | Preserving temp. (° C.) | Initial concentration maintained (%) | | | |
|---|---|---|---|---|---|---|
|  |  |  | 1 day later | 7 days later | 14 days later | 28 days later |
| Formulation 9 | Capsule containing retinol in Ex. 6 | 25 | 100 | 99 | 97 | 95 |
|  |  | 40 | 100 | 92 | 91 | 85 |
| Formulation 10 | Capsule containing coenzyme O-10 in Ex. 7 | 25 | 100 | 99 | 99 | 99 |
|  |  | 40 | 100 | 99 | 97 | 95 |
| Formulation 11 | Capsule containing tocopherol in Ex. 8 | 25 | 100 | 100 | 99 | 98 |
|  |  | 40 | 100 | 98 | 96 | 94 |
| Formulation 12 | Capsule containing retinol in Ex. 9 | 25 | 100 | 100 | 99 | 99 |
|  |  | 40 | 100 | 100 | 99 | 98 |
| Formulation 13 | Capsule containing coenzyme O-10 in Ex. 10 | 25 | 100 | 99 | 99 | 99 |
|  |  | 40 | 100 | 99 | 97 | 95 |
| Formulation 14 | Capsule containing tocopherol in Ex. 11 | 25 | 100 | 100 | 99 | 98 |
|  |  | 40 | 100 | 98 | 96 | 94 |
| Comp. Formulation 1 | Capsule containing retinol in Comp. Ex. 3 | 25 | 100 | 98 | 97 | 91 |
|  |  | 40 | 96 | 77 | 68 | 54 |
| Comp. Formulation 2 | Retinol | 25 | 98 | 93 | 78 | 60 |
|  |  | 40 | 85 | 67 | 51 | 40 |

The results of Table 5 confirm that the active ingredients such as retinol, coenzyme Q-10 and tocopherol loaded within the liquid crystal polymer microcapsules of the present invention can exhibit good stability in the cosmetic base after long terms of preservation. These results can be construed that active ingredients have similar molecular structure to that of liquid crystal material, so to have good compatibility, and thereby can be stabilized by fixation within molecular arrangement of liquid crystal. In addition, because polymethyl methacrylate polymer forming outer rind of microcapsule can serve as the first protector to external irritation, the stability can be more improved.

On the contrary, the retinol loaded in simple polymer particle of Comp. Example 3 cannot obtain fixation effect of liquid crystal. And, the polymer particles are swelled by water, oily ingredients or surfactants in cosmetic base, to easily contact with external environment and thereby to become unstable.

Such swelling of the particles can be obviously decreased by crosslinking the polymer. Consequently, the liquid crystal crosslinked polymer microcapsules of the present invention can efficiently block external irritation. In particular, the liquid crystal crosslinked polymer microcapsules obtained in Example 9 can improve the stability of the retinol loaded more than the crosslinked network of polymer by addition of crosslinking agent in Example 6.

EXPERIMENTAL EXAMPLE 5

In order to confirm the results of Experimental Example 4 by addition of the crosslinkable copolymer in another formulations, transparent gel type soluble formulations having the following composition of Table 6 and suspended emulsion type lotion having the following composition of Table 7 were prepared and tested in the same method described in the Experimental Example 4.

TABLE 6

| | Transparent gel type soluble formulations | | |
|---|---|---|---|
| Materials | Formulation 15 | Comp. Formulation 3 | Comp. Formulation 4 |
| Glycerin | 5 | 5 | 5 |
| Propylene glycol | 4 | 4 | 4 |
| Microcapsule | | | |
| Ex. 9 | 5 | — | — |
| Comp. Ex. 3 | — | 5 | — |
| Retinol (not-encapsulated) | — | — | 5 |
| Ethanol | 10 | 10 | 10 |
| Sodium polyacrylate | 0.5 | 0.5 | 0.5 |
| Preservative | q.s. | q.s. | q.s. |
| Distilled water | to 100 | to 100 | to 100 |

TABLE 7

Suspended emulsion type lotion

| Materials | Formulation 16 | Comp. Formulation 5 | Comp. Formulation 6 |
|---|---|---|---|
| Stearic acid | 2 | 2 | 2 |
| Cetyl alcohol | 2 | 2 | 2 |
| Lanolin alcohol | 2 | 2 | 2 |
| Liquid paraffin | 7 | 7 | 7 |
| Cyclomethicone | 5 | 5 | 5 |
| Polyoxyethylene monooleic ester | 2 | 2 | 2 |
| Preservative, Antioxidant | q.s. | q.s. | q.s. |
| Glycerine | 3 | 3 | 3 |
| Propylene glycol | 5 | 5 | 5 |
| Triethylamine | 1 | 1 | 1 |
| Microcapsule | | | |
| Ex. 9 | 8 | — | — |
| Comp. Ex. 3 | — | 8 | — |
| Retinol (not-encapsulated) | — | — | 8 |
| Sodium polyacrylate | 0.15 | 0.15 | 0.15 |
| Distilled water | to 100 | to 100 | to 100 |

The results are shown in Table 8.

TABLE 8

| | Microcapsule | Preserving temp. (° C.) | Initial concentration maintained (%) | | | |
|---|---|---|---|---|---|---|
| | | | 1 day later | 7 days later | 14 days later | 28 days later |
| Formulation 15 | Capsule containing retinol in Ex. 9 | 25 | 100 | 100 | 100 | 100 |
| | | 40 | 100 | 100 | 100 | 99 |
| Comp. Formulation 3 | Capsule containing retinol in Comp. Ex. 4 | 25 | 100 | 98 | 99 | 91 |
| | | 40 | 92 | 80 | 69 | 54 |
| Comp. Formulation 4 | Retinol | 25 | 98 | 95 | 88 | 63 |
| | | 40 | 89 | 65 | 52 | 33 |
| Formulation 16 | Capsule containing retinol in Ex. 9 | 25 | 100 | 100 | 100 | 100 |
| | | 40 | 100 | 100 | 98 | 97 |
| Comp. Formulation 5 | Capsule containing retinol in Comp. Ex. 3 | 25 | 99 | 97 | 97 | 93 |
| | | 40 | 95 | 75 | 63 | 49 |
| Comp. Formulation 6 | Retinol | 25 | 99 | 92 | 85 | 61 |
| | | 40 | 88 | 66 | 55 | 38 |

As shown in Table 8, the retinols loaded in the liquid crystal crosslinked polymer microcapsules of the present invention have good stability in gel type formulation or in emulsion type formulation.

As shown by the above description, because liquid crystal within polymer phase exhibits its unique behavior as it is, the thermotropic liquid crystal polymer microcapsules of the present invention are expected to be incorporated into cosmetic composition as a good additive for visual effect and to be applied to smart drug-delivery system having temperature dependence. In addition, because the present microcapsules can improve the stability of active ingredients loaded within liquid crystal, it can be applied as a stabilizing media for the active ingredients. Further, by external irritation-blocking property of polymer phase and good compatibility with organic compounds, the present invention will be applied to various field such as electronic materials, coating materials and paper stock utilizing unique behavior of thermotropic liquid crystal.

Although preferred embodiments of the present invention have been described in detail hereinabove, it should be clearly understood that many variations of the basic inventive concepts herein taught which may appear to those skilled in the art will still fall within the spirit and scope of the present invention as defined in the appended claims.

The invention claimed is:

1. A method for stabilizing an active ingredient by loading within thermotropic liquid crystal polymer microcapsules prepared by a method comprising the following steps of:
   (1) dissolving a thermotropic liquid crystal selected from the group consisting of cholesterol and cholesteryl derivatives and a monomer in a solvent and then adding an initiator thereto;
   (2) emulsifying the solution of step (1) in aqueous phase in the presence of a dispersion stabilizer; and
   (3) suspension polymerizing the emulsion of step (2) in the presence of a polymerization inhibitor, to give thermotropic liquid crystal polymer microcapsules having a structure of liquid crystal material surrounded by polymer;
   wherein a crosslinkable copolymer is obtained by copolymerizing said monomer of step (1) and a monomer having a crosslinkable functional group, and wherein said crosslinkable functional group is selected from the group consisting of trichlorovinylsilane, trimethoxyvinylsilane, triethoxyvinylsilane, vinyltriisopropoxysilane, vinyl tri-t-butoxysilane, vinyltriphenoxysilane, vinyltriacetoxysilane, vinyl tri (isobutoxy)silane, vinyl-tri (2-methoxyethoxy)silane, 8-oct-1-enyltrichlorosilane, 8-oct-1-enyltrimethoxysilane, 8-oct-1-enyltriethoxysilane, 6-hex-1-enyltrichlorosilane and 6-hex-1-enyltriethoxysilane;
   wherein the active ingredient is firstly stabilized in the thermotropic liquid crystal polymer microcapsules by fixation by molecular arrangement within the liquid crystal polymer microcapsules and doubly stabilized by polymer surrounding the liquid crystals in thermotropic liquid crystal polymer microcapsules.

2. The method according to claim 1, wherein said active ingredient is selected from the group consisting of retinol, retinyl acetate, retinyl palmitate, tocopherol, tocopheryl acetate, tocopheryl linolate, tocopheryl nicotinate, linoleic acid, coenzyme Q-10, resveratrol and a plant-extracted essential oil.

3. The method according to claim 1, wherein a crosslinking agent is added in said step (1) in an amount of 0.1~0.3% by weight based on the total weight of monomer.

4. The method according to claim 1, wherein a cationic monomer, anionic monomer or hydrophilic monomer is added in said step (1), to give hydrated microcapsules.

5. The method according to claim 1, wherein said thermotropic liquid crystal is used in an amount of 0.1~50% by weight based on the total weight of microcapsule particle.

6. The method according to claim 1, wherein said cholesteryl derivative is selected from the group consisting of cholesteryl octanoate, cholesteryl nonanoate, cholesteryl oleyl carbonate and cholesteryl isostearyl carbonate.

* * * * *